US012630582B2

(12) United States Patent
Richardson et al.

(10) Patent No.: US 12,630,582 B2
(45) Date of Patent: May 19, 2026

(54) METHOD FOR BIOMATERIAL PURIFICATION AND KITS THEREOF

(71) Applicant: Solventum Intellectual Properties Company, Maplewood, MN (US)

(72) Inventors: Kristopher E. Richardson, Inver Grove Heights, MN (US); Daniel J. O'Neal, St. Paul, MN (US); Jerald K. Rasmussen, Woodville, WI (US); Andrew W. Vail, Bayport, MN (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 1028 days.

(21) Appl. No.: 17/766,356

(22) PCT Filed: Nov. 24, 2020

(86) PCT No.: PCT/IB2020/061072
§ 371 (c)(1),
(2) Date: Apr. 4, 2022

(87) PCT Pub. No.: WO2021/105864
PCT Pub. Date: Jun. 3, 2021

(65) Prior Publication Data

US 2024/0059731 A1 Feb. 22, 2024

Related U.S. Application Data

(60) Provisional application No. 62/941,269, filed on Nov. 27, 2019.

(51) Int. Cl.
*C07K 1/32* (2006.01)
*C07K 1/34* (2006.01)

(52) U.S. Cl.
CPC . *C07K 1/32* (2013.01); *C07K 1/34* (2013.01)

(58) Field of Classification Search
CPC .................................... C07K 1/32; C07K 1/34
See application file for complete search history.

(56) References Cited

U.S. PATENT DOCUMENTS 8,328,023 B2 12/2012 Weiss
8,377,672 B2 * 2/2013 Rasmussen ............ B01D 15/00 536/25.4

(Continued)

FOREIGN PATENT DOCUMENTS

| | | |
|---|---|---|
| EP | 3274069 | 1/2018 |
| WO | WO 2011-109151 | 9/2011 |
| WO | WO 2016-153915 | 9/2016 |

OTHER PUBLICATIONS

Schwellenbach et al., Preparation and characterization of high capacity, strong cation-exchange fiber based absorbents, Journal of Chromatography A, pp. 92-106. (Year: 2016).*

(Continued)

*Primary Examiner* — Kathryn Elizabeth Limbaugh
(74) *Attorney, Agent, or Firm* — HYLTON-RODIC LAW PLLC

(57) ABSTRACT

Described herein is a method of purifying a target molecule from an aqueous biological composition, the method comprising: (a) contacting a cationic polymer and the aqueous biological composition to form a mixture comprising a bio-polymer complex and the target molecule in a liquid, wherein the bio-polymer complex has an average particle diameter of at least 45 micrometers, (b) adding the mixture to a filtering volume of a vessel, wherein the vessel comprises loosely packed staple fibers; (c) allowing the mixture to separate through the loosely packed staple fiber; and (d) collecting a filtrate comprising the target molecule.

19 Claims, 1 Drawing Sheet

(56) References Cited

U.S. PATENT DOCUMENTS

| | | | | |
|---|---|---|---|---|
| 8,435,776 | B2 * | 5/2013 | Rasmussen | C08L 83/08 536/25.4 |
| 8,459,470 | B2 | 6/2013 | Weiss | |
| 8,551,894 | B2 | 10/2013 | Seshadri | |
| 8,652,582 | B2 | 2/2014 | Bothof | |
| 8,945,896 | B2 | 2/2015 | Rasmussen | |
| 9,296,847 | B2 | 3/2016 | Rasmussen | |
| 9,302,208 | B2 | 4/2016 | Seshadri | |
| 9,821,276 | B2 | 11/2017 | Berrigan | |
| 10,005,814 | B2 | 6/2018 | Rasmussen | |
| 10,087,405 | B2 | 10/2018 | Swanson | |
| 2018/0066095 | A1 | 3/2018 | Vail | |
| 2018/0265542 | A1 | 9/2018 | Rasmussen | |

OTHER PUBLICATIONS

McNerney, "PDADMAC flocculation of Chinese hamster ovary cells: Enabling a centrifuge-less harvest process for monoclonal antibodies", mAbs, 2015, vol. 7, No. 2, pp. 412-428.

International Search report for PCT International Application No. PCT/IB2020/061072 mailed on Feb. 23, 2021, 4 pages.

* cited by examiner

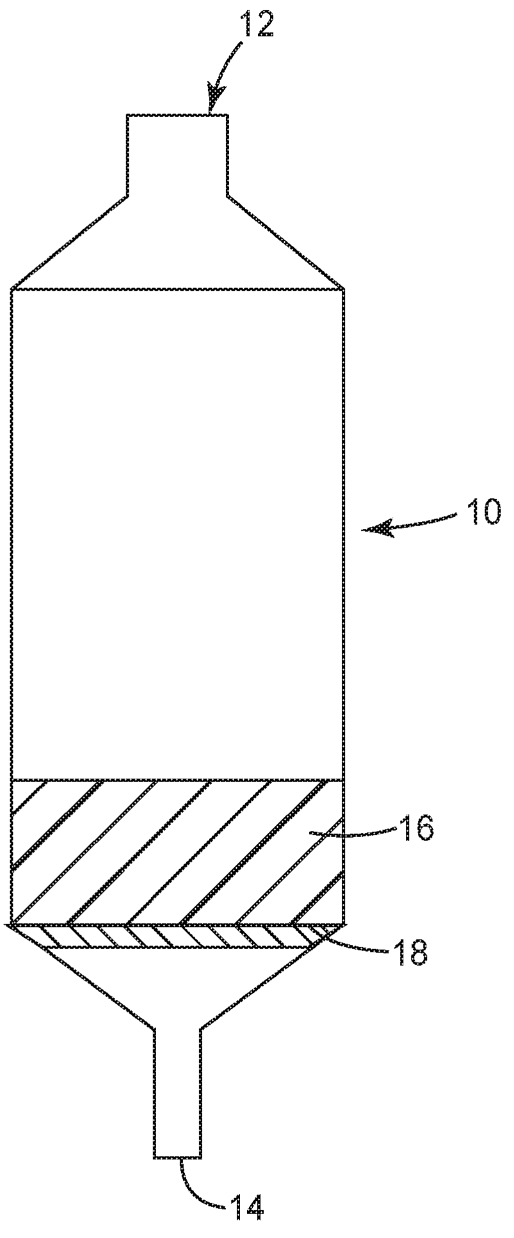
12
10
16
18
14

METHOD FOR BIOMATERIAL PURIFICATION AND KITS THEREOF

TECHNICAL FIELD

A method of separating a desired biological molecule (such as an antibody, protein, enzyme, etc.) from an aqueous biological composition (such as a harvest from a cell culture or fermentation process) is disclosed.

BACKGROUND

Manufacturing of large scale or commercial quantities of therapeutically useful targeted biomaterials, such as proteins, can be accomplished by growing cells that are engineered to produce a desired protein in bioreactors under controlled conditions. The technology used involves, for example, the fermentation of microorganisms which have been altered through recombinant DNA techniques or the culturing of mammalian cells which have been altered through hybridoma techniques. The cells are suspended in a broth which contains the salts, sugars, proteins, and various factors necessary to support the growth of particular cells. The desired product may be either secreted by the cells into the broth or retained within the cell body. The harvested broth is then processed to recover, purify, and concentrate the desired product.

SUMMARY

Typically, post-harvest processing of cell cultures and/or fermentation products involves a primary recovery step, which removes larger particle solids, cells and cell debris (typically by continuous centrifugation or microfiltration) and a secondary recovery step, which removes smaller sub-micron particles (typically a two-stage filtration train comprised of a depth filter followed by a membrane filter). After this recovery, the filtrate, comprising the targeted molecule is then exposed to extensive downstream processing, including column chromatography (such as protein A or cation-exchange) to yield high quantities of the purified target molecule.

Advances in manufacture of biomaterials have produced cell cultures having, for example higher antibody titers, which increases cell culture density and lengthens culture duration. This translates into higher levels of process-related impurities such as host cell proteins and DNA, lipids, colloids and cell debris. These higher impurity levels present challenges to the recovery, purification, and/or concentration of the target molecule. For example, the higher PCV (packed cell volume) concentrations can exceed the capacity of stack disk centrifugation and if the sub-micron cellular debris is not sufficiently removed, it can result in the fouling of downstream processes such as the depth filters and/or membrane filters.

Thus, there is need in the art for improved methods related to the recovery, isolation, and/or purification of targeted biomaterials such as proteins, enzymes and antibodies, involving procedures that are less time consuming, allow more efficient recovery of the desired product, and/or can be operated at lower pressure drops.

In one aspect, a method of purifying a non-binding target molecule from an aqueous biological composition comprising a binding species is disclosed, the method comprising:

(a) contacting a cationic polymer and the aqueous biological composition to form a mixture comprising a bio-polymer complex and the target molecule in a liquid, wherein the bio-polymer complex has an average particle diameter of at least 45 micrometers, (b) adding the mixture to a filtering volume of a vessel, wherein the vessel comprises loosely packed staple fibers;

(c) allowing the mixture to separate through the loosely packed staple fiber; and (d) collecting a filtrate comprising the target molecule.

In another aspect, a kit is disclosed, wherein the kit comprises a cationic polymer and a plurality of loosely packed staple fibers.

The above summary is not intended to describe each embodiment. The details of one or more embodiments of the invention are also set forth in the description below. Other features, objects, and advantages will be apparent from the description and from the claims.

BRIEF DESCRIPTION OF DRAWINGS

FIG. 1 is a cross-sectional view of an exemplary filtering vessel containing loosely packed staple fibers.

It should be understood that numerous other modifications and embodiments can be devised by those skilled in the art, which fall within the scope and spirit of the principles of the disclosure. The FIGURE may not be drawn to scale.

DETAILED DESCRIPTION

As used herein, the term

"Alkyl" means a linear or branched, cyclic or acyclic, saturated monovalent hydrocarbon having from one to about twelve carbon atoms (C1-C12), e.g., methyl, ethyl, 1-propyl, 2-propyl, pentyl, and the like.

"Alkylene" means a linear saturated divalent hydrocarbon having from one to about twelve carbon atoms (i.e., C1-C12) or a branched saturated divalent hydrocarbon having from three to about twelve carbon atoms (i.e., C3-C12), e.g., methylene, ethylene, propylene, 2-methylpropylene, pentylene, hexylene, and the like.

"Alkenyl" means a linear unsaturated monovalent hydrocarbon having from two to about twelve carbon atoms (i.e., C2-C12) or a branched unsaturated hydrocarbon having from three to about twelve carbon atoms (i.e., C3-C12).

"Aryl" means a monovalent aromatic, such as phenyl, naphthyl and the like.

"Guanidinyl" means a functional group selected from at least one of guanidine and biguanide.

(Hetero)alkyl includes alkyl and heteroalkyl groups, the later comprising one or more in-chain heteroatoms such as oxygen or nitrogen atoms. They can be linear or branched, cyclic or acyclic, saturated monovalent moeities having from one to about twelve carbon atoms.

(Hetero)alkylene includes divalent alkylene and heteroalkylene groups, the later comprising one or more in-chain heteroatoms such as oxygen or nitrogen atoms.

(Hetero)aryl includes aryl and heteroaryl groups, the later comprising one or more in-chain heteroatoms such as oxygen or nitrogen atoms.

(Hetero)arylene includes divalent aromatic arylene and heteroarylene groups, the later comprising one or more in-chain heteroatoms such as oxygen or nitrogen atoms.

"a", "an", and "the" are used interchangeably and mean one or more.

"and/or" is used to indicate one or both stated cases may occur, for example A and/or B includes, (A and B) and (A or B).

As used herein, recitation of ranges by endpoints includes all numbers subsumed within that range (e.g., 1 to 10 includes 1.4, 1.9, 2.33, 5.75, 9.98, etc.).

As used herein, recitation of "at least one" includes all numbers of one and greater (e.g., at least 2, at least 4, at least 6, at least 8, at least 10, at least 25, at least 50, at least 100, etc.).

As used herein, "comprises at least one of" A, B, and C refers to element A by itself, element B by itself, element C by itself, A and B, A and C, B and C, and a combination of all three.

The term "aqueous biological composition" refers to any aqueous composition comprising a desired macromolecule along with undesired macromolecules all of biological origin. The composition need not be exclusively of biological origin. In one embodiment, the aqueous biological composition is the harvest fluid of a fermentation or cell culture process.

The desired macromolecule of biological origin is the target molecule which is to be isolated and/or purified. Such target molecules include, for example, proteins such as enzymes, antibodies, or other desired proteins. Typically, the target molecule, also called the non-binding target molecule, is cationic in nature at the pH of the requisite fluid, such as the aqueous biological composition or an aqueous buffer solution. In one embodiment, the method of the present disclosure may be used in the separation of cationic proteins, more preferably monoclonal antibodies from the undesired components of a harvest fluid.

The aqueous biological composition also comprises a variety of near neutral or negatively charged macromolecules of biological origin, such as whole cells and insoluble cell debris, and soluble impurities, including protein impurities, such as host cell proteins, DNA, and chromatin, which need to be separated from the target molecule. These species are sometimes referred to as binding species due to their propensity to bind to cationic groups.

Cell debris generally refers to components of lysed (broken) cells, including the cell wall lipids, organelles (e.g., mitochondria, lysosomes, vesicles, and the like), and proteinaceous aggregates. Typically, cell debris are larger, predominantly negatively-charged material that can clog filters. Turbidity is one way to measure the concentration of cell debris in a fluid, where the higher the turbidity value the more cell debris present. For example, in one embodiment, the aqueous biological composition has a turbidity of at least 100, 200, 500, or even 1000 NTU (nephelometric turbidity unit) and at most 6000, 5000, 4000, 3000, or even 2000 NTU. In some embodiments, the solids content in the aqueous biological composition is so large that the turbidity cannot be measured.

Cells and cell debris, typically negatively charged, include those derived from archaea, bacteria, and eukaryotes. Bacteria include, but are not limited to, Gram-negatives such as *Pseudomonas* species, *Escherichia coli, Helicobacter pylori*, and *Serratia marcesens*; Gram-positives such as *Staphylococcus* species, *Enterococcus* species, *Clostridium* species, *Bacillus* species, and *Lactobacillus* species; bacteria that do not stain traditionally by Gram's method such as *Mycobacterium* species, and non-vegetative forms of bacteria such as spores. Eucaryotes include, but are not limited to, animal cells, algae, hybridoma cells, stem cells, cancer cells, plant cells, fungal hyphae, fungal spores, yeast cells, parasites, parasitic oocysts, insect cells, and helminthes. Proteins, include, but are not limited to, natural proteins, recombinant proteins, enzymes, and host cell proteins. Viruses include, but are not limited to, enveloped species such as Herpesviruses, Poxviruses, Adenoviruses, Papovaviruses, Coronaviruses, retroviruses such as HIV, and Plasmaviridae; and non-enveloped species such as Caliciviridae, Corticoviridae, Myoviridae, and Picornaviridae.

Undesired proteins having a near neutral or negative charge, such as protein impurities and host cell proteins, are also typically present in the aqueous biological composition. In one embodiment, the aqueous biological composition has a host cell protein concentration of at least 50,000; 100,000 or even 200,000 ng/mL and at most 2,000,000; 1,000,000; or even 500,000 ng/mL (nanograms/milliliter). These soluble proteins are smaller in nature and need to be separated from the target molecule.

DNA, is a nucleotide sequence, which is the blueprint for replication of the cell may also be present in the aqueous biological composition and is also negatively charged. In one embodiment, the aqueous biological composition has a concentration of DNA of at least $10^5$, $10^6$, $10^7$, $10^8$, or even $10^9$ picograms/mL.

These above referenced biological materials, including others such as bacterial spores, nucleic acids, endotoxins, and viruses, need to be separated from the target molecule before therapeutic use.

Typically, the aqueous biological composition is a buffered solution, which resists changes to pH. In one embodiment, the aqueous biological composition has a high salt concentration. The term "salt" is meant to include all low molecular weight ionic species which contribute to the conductivity of the solution. Many process solutions used in biopharmaceutical or enzyme manufacture have conductivities in the range of 15-30 mS/cm (milliSiemens per centimeter) (approximately 150-300 mM salt) or more.

In some embodiment, the aqueous biological composition has a packed cell volume of at least 5, 8, 10, or even 15 wt % and as high as 20 wt %.

The liquid portion of the aqueous biological composition is primarily water. Generally, the aqueous biological composition is substantially free (i.e., less than 1, 0.5, 0.1 or even 0.05 wt % or even none detectable) of organic solvents.

In one embodiment, the target molecule is present at a concentration of at least 0.1, 0.2, 0.5, 1, 2, 4, 6, or even 10 grams/liter (g/L) in the aqueous biological composition. In one embodiment, the desired macromolecules of biological origin are present at a concentration of at most 10, 12, 15, 18, or even 20 g/L in the aqueous biological composition. In some embodiments, the concentration of the desired macromolecules of biological origin is even higher than 20 g/L in the aqueous biological composition.

The present disclosure concerns a method of separating a targeted biological molecule from an aqueous biological composition. The primary and/or secondary recovery steps described above can be replaced by the methods disclosed herein, where a cationic polymer is used to flocculate near neutral and/or negatively charged biomaterials from an aqueous biological composition forming a bio-polymer complex. A bed of loosely packed stable fibers is then used to separate the bio-polymer complex from the aqueous liquid comprising the targeted biological molecule.

A cationic polymer is contacted with the aqueous biological composition. The cationic polymer comprises groups having the requisite affinity for binding near neutral or negatively charged macromolecules of biological origin, such as whole cells, cellular debris, host cell proteins, DNA, etc. which bind to the cationic polymer forming a bio-polymer complex.

The cationic polymer disclosed herein is water soluble or water dispersible. As used herein, the term "water soluble"

refers to a material that can be dissolved in water. The solubility is typically at least about 0.1 gram per milliliter of water. As used herein, the term "water dispersible" refers to a material that is not water soluble, but that can be emulsified or suspended in water. The cationic polymer also comprises a functional group attached (e.g., indirectly or directly covalently bonded) to the polymer backbone, wherein the functional group is a guanidinyl group which is sufficiently basic that it is substantially protonated in aqueous media having a pH of 5.0-8.0. For example, suitable such basic groups include groups with a $pK_a$ in water of their protonated cationic form of at least 9, preferably at least 10, and more preferably at least 12.5, or, meaning that the group is capable of being protonated by the water.

In one embodiment, the cationic polymer comprises at least one guanidinyl-containing side chain according to Formula (I):

$$[C(R^1){=}N{-}R^2]_n{-}N(R^3){-}[C({=}N{-}R^4)N(R^4)]_m{-}R^5 \quad (I)$$

In Formula (I), the group $R^1$ is hydrogen, C1-C12 (hetero) alkyl, or C5-C12 (hetero)aryl, or a residue of the polymer chain. The group $R^2$ is a covalent bond, a C2-C12 (hetero) alkylene, or a C5-C12 (hetero)arylene. The group $R^3$ is hydrogen, C1-C12 (hetero)alkyl, or C5-C12 (hetero)aryl, or can be a residue of the polymer chain when n is 0. Each group $R^4$ is independently hydrogen, C1-C12 (hetero)alkyl, or C5-C12 (hetero)aryl. The group $R^5$ is hydrogen, C1-C12 (hetero)alkyl, C5-C12 (hetero)aryl, or $-N(R^4)_2$. The variable n is equal to 0 or 1 depending on the precursor polymer used to form the guanidinyl-containing polymer. The variable m is equal to 1 or 2 depending on whether the cationic group is a guanidinyl or biguanidinyl group.

Most cationic polymers have more than one pendent guanidinyl-containing group. The number of pendent guanidinyl-containing groups can be varied depending the method used to prepare the cationic polymer. In some embodiments, the cationic polymer comprises at least 1, 2, 4, or even 5 pendent guanidinyl-containing groups. In some embodiments, the cationic polymer comprises at most 10, 20, 40, 60, 80, 100, 200, 500, or even 1000 pendent guanidinyl-containing groups.

The cationic guanidinyl-containing polymers may be derived from amino-containing polymers and/or carbonyl-containing polymers.

In some embodiments, the cationic polymer is prepared by reaction of an amino-containing polymer precursor with a guanylating agent. Such guanidinyl-containing polymers and how to make them may be found, for example, in U.S. Pat. No. 10,087,405 (Swanson et al.), herein incorporated by reference. When an amino-containing polymer is used, typically n in Formula (I) is 0.

Examples of amino-containing polymers suitable for use include, but are not limited to, polyvinylamine, poly(N-methylvinylamine), polyallylamine, polyallylmethylamine, polydiallylamine, poly(4-aminomethylstyrene), poly(4-aminostyrene), poly(acrylamide-co-methylaminopropylacrylamide), poly(acrylamide-co-aminoethylmethacrylate), polyethylenimine, polypropylenimine, polylysine, polyaminoamides, and polydimethylamine-epichlorohydrin-ethylenediamine.

Other useful amino-containing polymers that have primary or secondary amino end groups include, but are not limited to, dendrimers (hyperbranched polymers) formed from polyamidoamine (PAMAM) and polypropylenimine. Exemplary dendrimeric materials formed from PAMAM are commercially available under the trade designation STARBURST (PAMAM) dendrimer (e.g., Generation 0 with 4 primary amino groups, Generation 1 with 8 primary amino groups, Generation 2 with 16 primary amino groups, Generation 3 with 32 primary amino groups, and Generation 4 with 64 primary amino groups) from Aldrich Chemical (Milwaukee, WI). Dendrimeric materials formed from polypropylenimine are commercially available under the trade designation DAB-Am from Aldrich Chemical. For example, DAB-Am-4 is a generation 1 polypropylenimine tetraamine dendrimer with 4 primary amino groups, DAB-Am-8 is a generation 2 polypropylenimine octaamine dendrimer with 8 primary amino groups, DAB-Am-16 is a generation 3 polypropylenimine hexadecaamine with 16 primary amino groups, DAB-Am-32 is a generation 4 polypropylenimine dotriacontaamine dendrimer with 32 primary amino groups, and DAB-Am-64 is a generation 5 polypropylenimine tetrahexacontaamine dendrimer with 64 primary amino groups.

Examples of suitable amino-containing polymers that are biopolymers include chitosan as well as starch that is grafted with reagents such as methylaminoethylchloride.

Still other examples of amino-containing polymers include polyacrylamide homo- or copolymers and amino-containing polyacrylate homo- or copolymers prepared with a monomer composition containing an amino-containing monomer such as an aminoalkyl(meth)acrylate, (meth)acrylamidoalkylamine, and diallylamine.

Suitable commercially available amino-containing polymers include, but are not limited to, polyamidoamines that are available under the trade designations ANQUAMINE (e.g., ANQUAMINE 360, 401, 419, 456, and 701) from Air Products and Chemicals (Allentown, PA), polyethylenimine polymers that are available under the trade designation LUPASOL (e.g., LUPASOL FG, PR8515, Waterfree, P, and PS) from BASF Corporation (Resselaer, NY), polyethylenimine polymers such as those available under the trade designation CORCAT P-600 from EIT Company (Lake Wylie, SC), and polyamide resins such as those available from Cognis Corporation (Cincinnati, OH) under the traded designation VERSAMID series of resins that are formed by reacting a dimerized unsaturated fatty acid with alkylene polyamines.

In some embodiments, it may be advantageous to react the amino-containing polymer precursor to provide other ligands or groups in addition to the guanidinyl-containing group. For example, it may be useful to include a hydrophobic ligand, an ionic ligand, or a hydrogen bonding ligand.

The additional ligands can be readily incorporated into the amino-containing polymers by alkylation or acylation procedures well known in the art. For example, amino groups of the amino-containing polymer can be reacted using halide, sulfonate, and sulfate displacement reactions or using epoxide ring opening reactions. Useful alkylating agents for these reactions include, for example, dimethylsulfate, butyl bromide, butyl chloride, benzyl bromide, dodecyl bromide, 2-chloroethanol, bromoacetic acid, 2-chloroethyltrimethylammonium chloride, styrene oxide, glycidyl hexadecyl ether, glycidyltrimethylammonium chloride, and glycidyl phenyl ether. Useful acylating agents include, for example, acid chlorides and anhydrides such as benzoyl chloride, acetic anhydride, succinic anhydride, and decanoyl chloride, and isocyanates such as trimethylsilylisocyanate, phenyl isocyanate, butyl isocyanate, and butyl isothiocyanate. In such embodiments 0.1 to 20 mole percent, preferably 2 to 10 mole percent, of the available amino groups of the amino-containing polymer may be alkylated and/or acylated.

In some embodiments, the cationic polymer is prepared by reaction of a carbonyl-containing polymer and a suitable guanylating agent for reaction with a carbonyl group. Such carbonyl-containing polymers and how to make them maybe found, for example, in U.S. Pat. No. 10,087,405 (Swanson et al.), herein incorporated by reference.

When a carbonyl-containing polymer is used, typically n in Formula (I) is 1 and the polymer comprises a group of —C(O)—$R^1$, which can be reacted with a guanylating agent. The carbonyl group —C(O)—$R^1$ is an aldehyde group (when $R^1$ is hydrogen) or a ketone group (when $R^1$ is a (hetero)alkyl or (hetero)aryl). Although the carbonyl-group can be part of the polymeric backbone or part of a pendant group from the polymeric backbone, it is typically a pendant group.

In some embodiments, the carbonyl-containing polymer is the polymerized product of a monomer composition that includes an ethylenically unsaturated monomer having a carbonyl group, preferably a ketone group. Suitable monomers having a carbonyl group include, but are not limited to, acrolein, vinyl methyl ketone, vinyl ethyl ketone, vinyl isobutyl ketone, isopropenyl methyl ketone, vinyl phenyl ketone, diacetone (meth)acrylamide, acetonyl acrylate, and acetoacetoxyethyl (meth)acrylate.

In other embodiments, the carbonyl-containing polymer is the polymerized product of a monomer composition that includes carbon monoxide and one or more ethylenically unsaturated monomer (i.e., the carbonyl-containing polymer is a carbon monoxide copolymer). An example of a carbon monoxide containing copolymer is ELVALOY 741, a terpolymer of ethylene/vinyl acetate/carbon monoxide from DuPont (Wilmington, DE, USA).

In addition to carbon monoxide and/or an ethylenically unsaturated monomer with a carbonyl group (e.g., a ketone group), the monomer composition used to form that carbonyl-containing polymer can optionally further comprise ethylenically unsaturated hydrophilic monomer units. As used herein, "hydrophilic monomers" are those polymerizable monomers having water miscibility (water in monomer) of at least 1 weight percent preferably at least 5 weight percent without reaching a cloud point, and contain no functional groups that would interfere with the binding of biological substances to the ligand group. The carbonyl-containing polymer may include, for example, 0 to 90 weight percent of the hydrophilic monomers in the monomer composition. If present, the hydrophilic monomer can be present in an amount in a range of 1 to 90 weight percent, 1 to 75 weight percent, 1 to 50 weight percent, 1 to 25 weight percent, or 1 to 10 weight percent based on based a total weight of the monomer composition.

The hydrophilic groups of the hydrophilic monomers may be neutral and/or have a positive charge. Hydrophilic monomers with an ionic group can be neutral or charged depending on the pH conditions. Hydrophilic monomers are typically used to impart a desired hydrophilicity (i.e. water solubility or dispersibility) to the carbonyl-containing polymer.

Some exemplary hydrophilic monomers that are capable of providing a positive charge are amino (meth)acrylates or amino (meth)acrylamides of Formula (II) or quaternary ammonium salts thereof. The counter ions of the quaternary ammonium salts are often halides, sulfates, phosphates, nitrates, and the like.

(II)

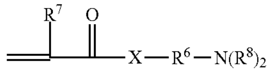

In Formula (II), the group X is oxy (i.e., —O—) or —$NR^3$— where $R^3$ is hydrogen, $C_1$-$C_{12}$ (hetero)alkyl, or $C_5$-$C_{12}$ (hetero)aryl. The group $R^6$ is a $C_2$ to $C_{10}$ alkylene, preferably a $C_2$-$C_6$ alkylene. The group $R^7$ is independently hydrogen or methyl. Each $R^8$ is independently hydrogen, alkyl, hydroxyalkyl (i.e., an alkyl substituted with a hydroxy), or aminoalkyl (i.e., an alkyl substituted with an amino). Alternatively, the two $R^8$ groups taken together with the nitrogen atom to which they are attached can form a heterocyclic group that is aromatic, partially unsaturated (i.e., unsaturated but not aromatic), or saturated, wherein the heterocyclic group can optionally be fused to a second ring that is aromatic (e.g., benzene), partially unsaturated (e.g., cyclohexene), or saturated (e.g., cyclohexane).

It will be understood with respect to Formula (II) that the depicted ethylenically unsaturated (meth)acryloyl group ($CH_2$=C($R^7$)—C(O)— group) may be replaced by another ethylenically unsaturated group of reduced reactivity, such as vinyl, vinyloxy, allyl, allyloxy, and acetylenyl.

In some embodiments of Formula (II), both $R^8$ groups are hydrogen. In other embodiments, one $R^8$ group is hydrogen and the other is an alkyl having 1 to 10, 1 to 6, or 1 to 4 carbon atoms. In still other embodiments, at least one of $R^8$ groups is a hydroxy alkyl or an amino alkyl that have 1 to 10, 1 to 6, or 1 to 4 carbon atoms with the hydroxy or amino group being positioned on any of the carbon atoms of the alkyl group. In yet other embodiments, the $R^8$ groups combine with the nitrogen atom to which they are attached to form a heterocyclic group. The heterocyclic group includes at least one nitrogen atom and can contain other heteroatoms such as oxygen or sulfur. Exemplary heterocyclic groups include, but are not limited to imidazolyl. The heterocyclic group can be fused to an additional ring such as a benzene, cyclohexene, or cyclohexane. Exemplary heterocyclic groups fused to an additional ring include, but are not limited to, benzoimidazolyl.

Exemplary amino acrylates (i.e., "X" in Formula (II) is oxy) include N,N-dialkylaminoalkyl (meth)acrylates such as, for example, N,N-dimethylaminoethyl(meth)acrylate, N,N-dimethylaminoethylacrylate, N,N-diethylaminoethylacrylate, N,N-dimethylaminopropyl(meth)acrylate, N-tert-butylaminopropyl(meth)acrylate, and the like.

Exemplary amino (meth)acrylamides (i.e., "X" in Formula (II) is —$NR^3$—) include, for example, N-(3-aminopropyl)methacrylamide, N-(3-aminopropyl)acrylamide, N-[3-(dimethylamino)propyl]methacrylamide, N-[3-(dimethylamino)propyl]acrylamide, N-(3-imidazolylpropyl)methacrylamide, N-(3-imidazolylpropyl)acrylamide, N-(2-imidazolylethyl)methacrylamide, N-(1,1-dimethyl-3-imidazolylpropyl)methacrylamide, N-(1,1-dimethyl-3-imidazolylpropyl)acrylamide, N-(3-benzimidazolylpropyl)acrylamide, and N-(3-benzimidazolylpropyl)methacrylamide.

Exemplary quaternary salts of the monomers of Formula (II) include, but are not limited to, (meth)acrylamidoalkyltrimethylammonium salts (e.g., 3-methacrylamidopropyltrimethylammonium chloride and 3-acrylamidopropyltrimethylammonium chloride) and (meth)acryloxyalkyltrimethylammonium salts (e.g., 2-acryloxyethyltrimethylammonium chloride, 2-methacryloxyethyltrimethylammonium chloride, 3-methacryloxy-2- hydroxypropyltrimethylammonium chloride, 3-acryloxy-2-hydroxypropyltrimethylammonium chloride, and 2-acryloxyethyltrimethylammonium methyl sulfate).

Other monomers that can provide positively charged groups to the polymer include the dialkylaminoalkylamine adducts of alkenylazlactones (e.g., 2-(diethylamino)ethylamine, (2-aminoethyptrimethylammonium chloride, and 3-(dimethylamino)propylamine adducts of vinyldimethylazlactone) and diallylamine monomers (e.g., diallylammonium chloride and diallyldimethylammonium chloride).

In some preferred embodiments, the optional hydrophilic monomer may have an ethylenically unsaturated group such as a (meth)acryloyl group and a poly(alkylene oxide) group. For example, the hydrophilic monomer can be a poly (alkylene oxide) mono(meth)acrylate compounds, where the terminus is a hydroxy group, or an alkyl ether group. Such monomers are of the general Formula (III).

$$R^9—O—(CH(R^9)—CH_2—O)_p—C(O)—C(R^9)=CH_2 \quad (III)$$

In Formula (III), each $R^9$ is independently hydrogen or a $C_1$-$C_4$ alkyl. The variable p is at least 2 such as, for example, 2 to 100, 2 to 50, 2 to 20, or 2 to 10.

In one embodiment, the carbonyl containing polymer comprises a poly(alkylene oxide) group (depicted as $—(CH(R^9)—CH_2—O)_p—$), wherein the poly(alkylene oxide) group is a poly(ethylene oxide). In another embodiment, the poly(alkylene oxide) group is a poly(ethylene oxide-co-propylene oxide). Such copolymers may be block copolymers, random copolymers, or gradient copolymers.

Other representative examples of suitable hydrophilic monomers include but are not limited to 2-hydroxyethyl (meth)acrylate; N-vinylpyrrolidone; N-vinylcaprolactam; acrylamide; mono- or di-N-alkyl substituted acrylamide; t-butyl acrylamide; dimethylacrylamide; N-octyl acrylamide; poly(alkoxyalkyl) (meth)acrylates including 2-(2-ethoxyethoxy)ethyl (meth)acrylate, 2-ethoxyethyl (meth) acrylate, 2-methoxyethoxyethyl (meth)acrylate, 2-methoxyethyl methacrylate, polyethylene glycol mono (meth)acrylates; alkyl vinyl ethers, including vinyl methyl ether; and mixtures thereof. Preferred hydrophilic monomers include those selected from the group consisting of dimethylacrylamide, 2-hydroxyethyl (meth)acrylate, and N-vinylpyrrolidinone.

In some embodiments, the monomer composition used to form the carbonyl-containing polymer can optionally include a hydrophobic monomer. As used herein, the term "hydrophobic monomer" refers monomers having a water miscibility (water in monomer) that is less than 1 weight percent. The hydrophobic monomers can be used in amounts that do not deleteriously affect the binding performance of the guanidinyl-containing monomer polymer and/or the water dispersibility of the guanidinyl-containing polymer. When present, the hydrophobic monomer is typically present in an amount in a range of 1 to 20 weight percent, 1 to 10 weight percent, or 1 to 5 weight percent based on a total weight of monomers in the monomer composition.

Useful classes of hydrophobic monomers include alkyl acrylate esters and amides, exemplified by straight-chain, cyclic, and branched-chain isomers of alkyl esters containing $C_1$-$C_{30}$ alkyl groups and mono- or dialkyl acrylamides containing $C_1$-$C_{30}$ alkyl groups. Useful specific examples of alkyl acrylate esters include: methyl acrylate, ethyl acrylate, n-propyl acrylate, n-butyl acrylate, iso-amyl acrylate, n-hexyl acrylate, n-heptyl acrylate, isobornyl acrylate, n-octyl acrylate, iso-octyl acrylate, 2-ethylhexyl acrylate, iso-nonyl acrylate, decyl acrylate, undecyl acrylate, dodecyl acrylate, lauryl acrylate, tridecyl acrylate, and tetradecyl acrylate. Useful specific examples of alkyl acrylamides include mono- and dialkylacrylamides having pentyl, hexyl, heptyl, isobornyl, octyl, 2-ethylhexyl, iso-nonyl, decyl, undecyl, dodecyl, tridecyl, and tetradecyl groups may be used. The corresponding methacrylate esters may be used.

Additional useful classes of hydrophobic monomers further include vinyl monomers such as vinyl acetate, styrenes, and alkyl vinyl ethers, and maleic anhydride.

The guanidinyl-containing polymers comprising the side chain according to Formula (I) are often the reaction product of a carbonyl-containing polymer precursor and a guanylating agent of Formula (IV).

(IV)

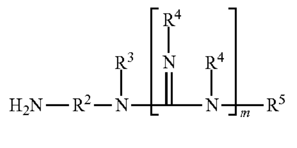

In Formula (IV), the group $R^2$ is a covalent bond, $C_2$-$C_{12}$ (hetero)alkylene, or $C_5$-$C_{12}$ (hetero)arylene. Group $R^3$ is hydrogen, $C_1$-$C_{12}$ (hetero)alkyl, or $C_5$-$C_{12}$ (hetero)aryl. Each $R^4$ is independently hydrogen, $C_1$-$C_{12}$ (hetero)alkyl, or $C_5$-$C_{12}$ (hetero)aryl. Group $R^5$ is H, $C_1$-$C_{12}$ (hetero)alkyl, or $C_5$-$C_{12}$ (hetero)aryl, or $—N(R^4)_2$. The variable m is equal to 1 or 2.

For ease of description, the carbonyl-containing polymer can be represented by the formula Polymer-C(=O)—$R^1$. The carbonyl group can be in the backbone or in a pendant group but is usually in a pendant group. When reacted with a guanylating agent of Formula (IV), the carbonyl group in the carbonyl-containing polymer undergoes a condensation reaction with a terminal amine group of the guanylating agent. The guanidinyl-containing polymer typically has guanidinyl-containing pendant groups of Formula (V).

(V)

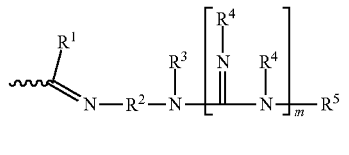

The groups $R^2$, $R^3$, $R^4$, and $R^5$ are the same as described above for Formula (IV) and the wavy line represents the polymer. The group of formula

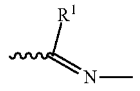

in Formula (V) is the linkage formed between the terminal amine of the ligand compound of Formula (IV) and the carbonyl group of the carbonyl-containing polymer. The wavy line denotes the attachment site of the group via a covalent bond to the rest of the polymer. Group $R^1$ is hydrogen (when the carbonyl group is an aldehyde group), C1-C12 (hetero)alkyl (when the carbonyl group is a ketone group and the ketone group is part of a pendant group), or C5-C12 (hetero)aryl (when the carbonyl group is a ketone group and the ketone group is part of a pendant group), or a residue of the polymer chain (when the carbonyl group is a group in the backbone of the carbonyl-containing polymer). In most embodiments, the group of Formula (V) is part of a pendant group of the guanidinyl-containing polymer.

In other embodiments, the guanidyl-containing polymer may be prepared in which the imine linking group (~~C($R^1$)=N—) is reduced to an amine linking group (~~CH($R^1$)—NH—). This may be affected by treating the extant ligand functional polymer with a reducing agent, such as sodium cyanoborohydride, or the reduction may be effected in situ by adding the reducing agent to the reaction mixture of the carbonyl functional (co)polymer and the compound of Formula V.

In many embodiments, some but not all of the carbonyl groups of the carbonyl-containing polymer are reacted with the guanylating agent of Formula (IV). Typically, at least 0.1 mole percent, at least 0.5 mole percent, at least 1 mole percent, at least 2 mole percent, at least 10 mole percent, at least 20 mole percent, or at least 50 mole percent of the carbonyl groups in the carbonyl-containing polymer precursor are reacted with the guanylating agent. Up to 100 mole percent, up to 90 mole percent, up to 80 mole percent, or up to 60 mole percent of the carbonyl groups can be reacted with the guanylating agent. For example, the guanylating agent can be used in amounts sufficient to functionalize 0.1 to 100 mole percent, 0.5 to 100 mole percent, 1 to 90 mole percent, 1 to 80 mole percent, 1 to 60 mole percent, 2 to 50 mole percent, 2 to 25 mole percent, or 2 to 10 mole percent of the carbonyl groups in the carbonyl-containing polymer.

Rather than reacting a precursor polymer with a guanylating agent to prepare a guanidinyl-containing polymer, the guanidinyl-containing polymer can be prepared by free radical polymerization of a guanidinyl-containing monomer, which refers to a monomer having an ethylenically unsaturated group and a guanidinyl-containing group. Example guanidinyl-containing monomers are of Formula (VI) and (VII).

(VI)

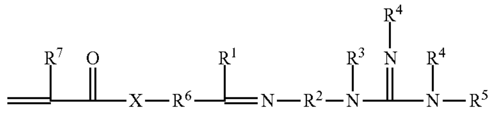

(VII)

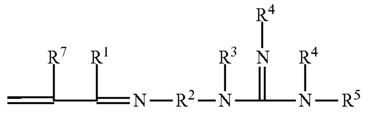

In Formulas (VI) and (VII), group $R^1$ is hydrogen, C1-C12 alkyl, or C5-C12 (hetero)aryl. Group $R^2$ is a covalent bond, a C2 to C12 alkylene, a C5-C12 (hetero)arylene, a divalent group of formula

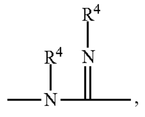

or a divalent group of formula

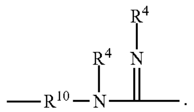

Group $R^{10}$ is C2 to C12 alkylene, or C5-C12 (hetero)arylene. Each $R^3$ is independently hydrogen, hydroxyl, C1-C12 alkyl, or C5-C12 (hetero)aryl. $R^3$ is preferably hydrogen or C1-C4 alkyl. Group $R^4$ is hydrogen, C1-C12 alkyl, C5-C12 (hetero)aryl, or —$N(R^3)_2$, wherein $R^3$ is independently hydrogen, hydroxyl, C1-C12 alkyl, or C5-C12 (hetero)aryl. Preferably, $R^4$ is hydrogen or C1-C4 alkyl. Group X is oxy or —$NR^3$—, wherein $R^3$ is hydrogen, hydroxyl, C1-C12 alkyl, or C5-C12 (hetero)aryl. Group $R^6$ is a C2 to C12 alkylene. Group $R^7$ is hydrogen or CH 3.

The amount of cationic polymer that is added relative to the amount of aqueous biological composition can vary over a wide range. In one embodiment, the amount of cationic polymer added to the aqueous biological composition is at least 0.01, 0.02, 0.05, 0.1, 0.5, 1, 5, 10, 20, 50, 100, 250, or even 500 micrograms/mL. In one embodiment, the amount of cationic polymer added to the aqueous biological composition is at most 50, 100, 250, 500, 1000, 2000, 5000, 7500, or even 10000 micrograms/mL. The optimal amount of cationic polymer added will depend upon the concentration of the near neutral or negatively charged biomaterials present (i.e., binding species) in the aqueous biological composition. Typically, the amount of cationic polymer relative to the amount of binding species will be in the range of 0.01% to 100% by weight, preferably 0.05%-30% by weight, more preferably about 0.1%-10% by weight. In one embodiment, the amount of cationic polymer added to the aqueous biological composition is less than the amount needed when the cationic polymer is on a carrier, such as a fiber.

The cationic polymer is contacted with the aqueous biological composition for a time sufficient for the near neutral and negatively charged binding species to interact with the cationic polymer to form a bio-polymer complex. The cationic polymer binds (for example ionically, hydrogen bonding, etc.) with the near neutral or negatively charged macromolecules. In one embodiment, the aqueous biological composition and the cationic polymer are agitated while they are in intimate contact with each other to form the bio-polymer complex. Suitable mixing methods include shaking by hand, laboratory agitators, mechanical and/or magnetic stirrers, and passing through a static mixer, for example. Agitation may be performed for any length of time sufficient to effectively bind biological compounds to the cationic polymer and may depend on the volume of material agitated. In some embodiments, the agitation is preferably less than 60 seconds, less than 45 seconds, or even less than 30 seconds. In other embodiments, the agitation may be as long as 20 minutes or more, for example.

The resulting mixture comprises the bio-polymer complex and the target molecule in an aqueous solution/suspension. In one embodiment, the target molecule may be disposed (dissolved or suspended) in the solution when the solution comprises from at least 50, 60, 70, 80, 90 or even 100 mM salt; and at most 125, 150, 200, 250, 300, 350, or even 400 mM salt.

In many embodiments, the cationic polymer, being positively charged in aqueous media, will bind near neutral or negatively charged species to the cationic functional group while other species (e.g., positively charged proteins such as monoclonal antibodies) will be excluded or repelled from the cationic polymer. In addition, the cationic polymer may be derived from one or more ionic monomers. In particular, the cationic polymer may comprise additional ionic groups that are positively charged at the selected pH of the aqueous biological solution to enhance electrostatic charge repulsion of proteins, such as monoclonal antibodies, many of which are charged positive at neutral pH.

The bio-polymer complex has an average particle diameter of at least 45, 50, 60, 70, 75 or even 80 micrometers. In one embodiment, the bio-polymer complex has an average particle diameter of at most 100, 110, 120, 130, 140, 150, 160, 170, 180, 190, 200, 220, 240, 260, 280, 300, 350, 400, 450, 500, or even 1000 micrometers. The average particle diameter may be determined using techniques known in the art such as reflectance. Typically, the resulting bio-polymer complex is not soluble in water and precipitates out of an aqueous solution.

In one embodiment, the bio-polymer complex is allowed to settle (for example via gravity over a period of time, or mechanical separations such as centrifugation) and the clarified aqueous portion can then be filtered as described below to separate the target molecule from the bio-polymer complex.

In another embodiment, the bio-polymer complex is suspended in an aqueous solution using techniques known in the art, such as mechanical agitation. Following suspension, the aqueous mixture then is subsequently (for example, immediately) filtered as described below to separate the target molecule from the bio-polymer complex.

In one embodiment, the mixture comprising the aqueous biological solution and the cationic polymer is substantially free of fibers, meaning the mixture, prior to the addition to the separation vessel, comprises less than 1, 0.5, or even 0.1% by weight or even no fibers versus the weight of the mixture, wherein a fiber is not water soluble and has a length of at least 100 nm. Exemplary fibers can include those fiber types disclosed below.

The aqueous portion or mixture is added to the filtering volume of a vessel. As shown in FIG. 1, vessel 10 comprises inlet 12 and outlet 14 defining a liquid flow path therebetween. A bed of loosely packed staple fibers 16 is positioned in the liquid flow path between the inlet and outlet, optional support 18 may be included downstream of the staple fibers. The optional support may be a frit or mesh used solely for supporting the staple fiber bed (such as sintered metal, glass or polymer, or a metal or polymeric mesh); or the optional support may be for example, a microporous membrane, a nonwoven, a woven fabric, which could provide further isolation of the target molecule; or combinations of the aforementioned. The mixture comprising the bio-polymer complex and the target biological molecule in a liquid is added to the inlet and allowed to interact with the loosely packed fibers. The clarified liquid (or filtrate), containing the target macromolecule, exits via the outlet.

The loosely packed fibers are staple fibers; that is, they are not continuous fibers. Preferably, the fibers have a length of at least 0.1, 0.3, or even 0.5 mm; and at most 2, 3, 4, or even 5 mm; however, other lengths may also be used. The fibers may be crimped or not crimped and/or fibrillated, for example.

As used herein, the term "loose" as applied to staple fiber means that the fiber is not formed into a paper, fabric, or twisted filament bundle (e.g., thread, yarn, or rope). The fibers may, however, be clumped together, although this is typically less preferred.

Suitable fibers include fibers comprising synthetic polymers such as polyolefins (e.g., polyethylene, polypropylene, copolymers of ethylene and propropylene, poly(l-butene), styrene-butadiene copolymers, polystyrene, and polyisobutylene, and combinations thereof); fluorinated polymers (e.g., poly(vinyl fluoride), poly(vinylidene), copolymers of vinylidene difluoride such as poly(vinylidene fluoride-co-hexafluompropylene), copolymers of tetrafluoroethylene, copolymers of chlorotrifluomethylene such as poly(ethylene-co-chlorotrifluoroethylene), combinations thereof, and copolymers of the foregoing with polyethylene and/or polypropylene); chlorinated polymers (e.g., polyvinylidene dichloride, polychloroprene, and polyvinyl chloride); polyesters (e.g., polycaprolactone and polyethylene terephthalate), polyamides poly(iminoadipoyliminohexamethylene), poly(iminoadipoyliminodecamethylene), and polycaprolactam); vinyl acetate homopolymers and copolymers (e.g., with ethylene), and hydrolyzed derivatives thereof (e.g., poly(vinyl alcohol) including, poly(ethylene-co-vinyl alcohol)); polyether sulfone); such as poly(diphenylether sulfone) and poly(diphenylsulfone-co-diphenylene oxide sulfone); and polyimides such as poly(pyromellitimide) One preferred synthetic fiber is fibrillated high-density polyethylene (HDPE); for example, fibrillated HDPE fibers available from MiniFibers, Inc., Johnson City, Tennessee, under the trade designation SHORT STUFF FIBRILLATED HDPE (e.g., in grades ESS2F, ESS5F, ESS50F, E380F, E505F, E780F, E990F). Useful natural fibers include rayon, cellulose, cotton, linen, chitosan, and starch.

The staple fibers are loosely packed in order to achieve efficient collection of the bio-polymer complex without excessively impeding fluid flow therethrough. The loose staple fibers may be packed into a separation vessel or the loose staple fibers may be pre-formed with the specified packing density into a shape or bed of fibers, such as a disk, or cartridge, which is then placed in the separation vessel. In one embodiment, the loosely packed staple fibers have a packing density of at least 0.01, 0.02, 0.03, 0.04, 0.05, 0.08, or even 0.10 $g/cm^3$. In one embodiment, the loosely packed staple fibers have a packing density of at most 0.15, 0.18, 0.20, 0.22, or even 0.23 $g/cm^3$. If the packing density is not dense enough the bio-polymer complex will pass through the staple fibers resulting in a filtrate with higher turbidity and inadequate clarification. If the packing density is too dense, the bio-polymer complex may form a layer or cake at the head of the filter bed resulting in the inability to pass fluid through the filter bed and/or an increase in the inlet pressure. As will be described in more detail below, in one embodiment, the staple fibers may comprise functionalization, which can bind biological species not captured in the bio-polymer complex. In such instances, there may be a preference for the separation vessel to comprise at least 1 g of loosely packed staple fibers per 50 g of the aqueous biological composition.

In one embodiment, the loosely packed staple fibers are treated with a cationic functional group to bind near neutral or negatively-charged species, which were not complexed by the cationic polymer. In one embodiment, the cationic functional group of the staple fiber is different from the cationic functional group of the cationic polymer.

The staple fibers can be cationically functionalized by grafting, for example, an acrylic polymer to the staple fibers according to known methods. The acrylic polymer can be made by polymerization of at least one acrylic monomer, optionally with at least one free-radically polymerizable monomer that is not an acrylic monomer. In one embodiment, the acrylic polymer grafted onto the surface of the fiber comprises at least 10, 20, 30, 40 or even 50 percent and at most 55, 60, 70, 80, 90 or even 100 percent by weight of a cationic or cationically-ionizable monomer unit. Free-radically polymerizable multifunctional monomers (e.g., having two or more free-radically polymerizable groups) may be included as well so long as the fibers do not become so tightly crosslinked that they no longer achieve the packing density recited herein. However, if the fibers become too crosslinked, steps, such as mechanical breaking can be used to mitigate the clumping. The multifunctional monomers may be monomers having at least two free-radically polymerizable groups, or these may have a single free-radically polymerizable group and another polymerizable group (e.g., an epoxy group) that can be reacted in a subsequent step after polymerization.

Examples of free-radically polymerizable acrylic monomers include (meth)acrylamide, dimethyl(meth)acrylamide, 2-hydroxyethyl(meth)acrylamide, 2-hydroxyethyl (meth) acrylate, glycidyl (meth)acrylate, 2-hydroxypropyl (meth) acrylamide, di(ethylene glycol)methyl ether (meth)acrylate, poly(ethylene glycol)(meth)acrylates, poly(propylene glycol)(meth)acrylates, 2-ethyxyethyl (meth)acrylate, n-ethyl methacrylamide, n-propyl acrylamide, 2-hydroxypropyl (meth)acrylamide, N-hydroxypropyl(meth)acrylate, 2-hydroxy-3-phenoxypropyl(meth)acrylate, tetrahydrofurfuryl (meth)acrylate, N-vinyl compounds such as, for example, N-vinylformamide, N-vinylpyrrolidone, and N-vinylcaprolactam, and cationic or cationically-ionizable, free-radically polymerizable acrylic monomers such as, for example, 3-(Methacryloylamino)propylltrimethylammonium chloride, 3-Acrylamidopropyl)trimethylammonium chloride, 2-(Methacryloyloxy)ethyl]trimethylammonium chloride, 3-methacryloxy-2-hydroxypropyltrimethylammonium chloride, 3-acryloxy-2-hydroxypropyltrimethylammonium chloride, 2-acryloxyethyltrimethylammonium methyl sulfate, 2-(Acryloyloxy)ethyl]trimethylammonium chloride, N-[3-(Dimethylamino)propyl]methacrylamide, 2-(Dimethylamino)ethyl methacrylate, 2-(Dimethylamino)ethyl acrylate, 2-Aminoethylmethacrylamide hydrochloride, 2-Aminoethyl methacrylate hydrochloride, and the IEM-Agmatine adduct as described in U.S. Pat. No. 8,652,582 (Bothof et al.), herein incorporated by reference. Acidic monomers such as acrylic acid, methacrylic acid, and (meth) acrylamidopropylsulfonic acid may also be used, but these may tend to interfere with performance of the cationically functionalized staple fibers and/or cause clumping of the fibers, and should typically be used judiciously, if at all, although this is not a requirement. Those monomers that are more hydrophilic or water soluble may be preferred in some embodiments due to their compatibility or solubility characteristics with the cationic or cationically-ionizable group containing acrylic monomer.

In one embodiment, useful free-radically polymerizable non-acrylic monomers may contain a cation or cationically-ionizable group. In such cases, no acrylic monomer having a cationic or cationically-ionizable group is needed to form the grafted acrylic polymer.

Exemplary such free-radically polymerizable non-acrylic monomers include those represented by the formula

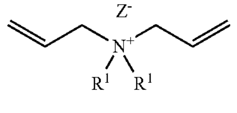

wherein $R^1$ is H or an alkyl group having from 1 to 4 carbon atoms (e.g., methyl, ethyl, propyl, isopropyl, butyl), and $Z^-$ is a non-interfering anion (e.g., an anion that will not cause agglomeration of the cationic ligand-functionalized staple fibers or that tightly binds to the quaternary nitrogen atom, or that is oxidative toward the biological composition), preferably having a charge of −1, −2, or −3, more preferably −1. Preferred non-interfering anions include chloride and bromide.

Examples of free-radically polymerizable multifunctional monomers include glycidyl (meth)acrylate, methylenebis (meth)acrylamide, bis(meth)acryloylpiperazine, ethylene glycol di(meth)acrylate, diethylene glycol di(meth)acrylate, ethoxylated (10) bisphenol A di(meth)acrylate ethoxylated (30) bisphenol A di(meth)acrylate, polyethylene glycol (200) di(meth)acrylate, polyethylene glycol (400) di(meth) acrylate, polyethylene glycol (600) di(meth)acrylate, tetraethylene glycol di(meth)acrylate, triethylene glycol di(meth) acrylate, and combinations thereof. Again, for compatibility or solubility reason, the hydrophilic or water soluble multifunctional monomers are preferred.

If included, the amount of multifunctional monomer is typically less than 5 percent by weight of the free-radically polymerizable monomers used to make the grafted acrylic polymer, preferably less than 2 percent by weight, and more preferably less than 1 percent by weight; however, this is not a requirement.

The grafted acrylic polymer may further comprise 0.1 to 90 percent by weight of at least one nonionizable hydrophilic monomer unit, or it may contain none at all. For example, the grafted acrylic polymer may contain at least 1 percent by weight, at least 5 percent by weight, at least 10 percent by weight, at least 15 percent by weight, or at least 25 percent by weight up to 30 percent by weight, 40 percent by weight, 50 percent by weight, 75 percent by weight, or 90 percent by weight of the at least one nonionizable hydrophilic monomer unit. In some embodiments, the nonionizable hydrophilic monomer unit comprises a divalent residue of an N-vinyllactam having from 5 to 7 carbon atoms as shown below, wherein n=1, 2, or 3.

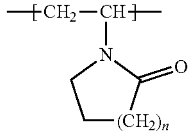

Such monomeric units can be readily introduced by including N-vinylpyrrolidone, N-vinylvalerolactam, and/or N-vinylcaprolactam in the monomers that are polymerized to prepare the grafted acrylic polymer.

In some embodiments, the nonionizable hydrophilic monomer unit comprises a divalent residue of a polyether (meth)acrylate as shown below, wherein $R^1$ and $R^3$ are as previously defined and w is an integer≥2.

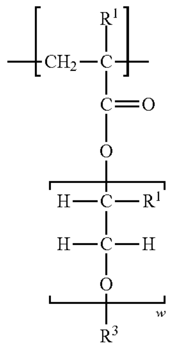

Such monomeric units can be readily introduced by including polyether (meth)acrylates in the monomers that are polymerized to prepare the grafted acrylic polymer. Methods of making such monomers are well-known in the art and many are commercially available. Examples include 2-(2-ethoxyethoxy)ethyl acrylate, methoxypolyethylene glycol (350) monoacrylate, methoxypolyethylene glycol (350) monomethacrylate, methoxypolyethylene glycol (550) monoacrylate, and methoxypolyethylene glycol (550) monomethacrylate, all available from Sartomer Co., Exton, Pennsylvania.

In one embodiment, a surfactant or compatibilizing agent may be used in the grafting of the fibers to promote wetting of the fibers by aqueous solutions. Exemplary surfactants and/or compatibilizing agents include, but are not limited to, polyethyleneglycol 200; polyethyleneglycol 400; glyceryl monoisostearate; polyethylene glycol dicaprylate/caprate (available under the trade designation ESTOL 1526 from Croda Inc., Edison, NJ); a non-ionic surfactant available under the trade designation SPAN 80 from TCI America, Portland, OR; polyethylene glycol trimethylnonyl ether; a non-ionic surfactant, available under the trade designation TERGITOL TMN-10 from Dow, Midland, MI; a surfactant available under the trade designation BRIJ L4-LQ-AP from Croda Inc., Edison, NJ; methoxypolyethylene glycol (available under the trade designation CARBOWAX 750 from Dow, Midland, MI); nonionic triblock copolymers known as poloxamers, which comprise a central hydrophobic block of polyoxypropylene sandwiched between two hydrophilic blocks of polyoxyethylene under the trade designation Pluronic from BASF; a conditioning agent for hair care available under the trade designation ABILQUAT 3272 (Goldschmidt Chemical Corp, Hopewell, VA); lauryl pyrrolidone; alkyl polyglucosides available under the trade designations GLUCOPON and PLANTACARE from BASF, Florham Park, NJ; sorbitan isostearate (available under the trade designation SPAN 120 LQ from Croda Inc., Edison, NJ; and a polyoxyethylene sorbitan fatty acid ester available under the trade designation NIKKOL TL-40 from Nikko Chemicals, Tokyo, Japan.

Separation of the target molecule from the bio-polymer complex is accomplished by entrapment of the biopolymer complex within the loosely packed staple fibers, which may serve to mechanically remove particulate debris remaining in the purified biological composition. The liquid having passed through the fibers, herein referred to as the filtrate, is collected. The filtrate, comprising the target molecule can then be further treated to isolate and/or concentrate the target molecule.

The aqueous biological solution often comprises buffers, electrolytes, and/or sugars needed for cell growth or fermentation, but these components can impact the performance of the traditional filters used in recovery and isolation of the target molecule and thus, the process solution (e.g., the aqueous biological solution) is diluted to decrease the ionic concentration. In one embodiment of the present disclosure, there is no dilution of the aqueous biological solution prior to contact with the cationic polymer and/or contact with the bed of loose staple fibers.

It has been discovered in the present application that the combination of particle size of the bio-polymer complex with the loosely packed staple fibers, allows for the high capacity separation of cell debris and other near neutral or negatively charged components in the aqueous biological composition from the target biological molecule, a high capacity for substantial reduction of DNA from the fluid, and/or a high degree of host cell protein reduction while also minimizing the number of process steps.

In one embodiment, the method of the present disclosure enables clarification of the aqueous biological composition, yielding a filtrate having a turbidity of less than 20, 15, 10, 5, or even 4 NTU.

EXAMPLES

Unless otherwise noted, all parts, percentages, ratios, etc. in the examples and the rest of the specification are by weight, and all reagents used in the examples were obtained, or are available, from general chemical suppliers such as, for example, Sigma-Aldrich Company, Saint Louis, Missouri, or may be synthesized by conventional methods.

The following abbreviations are used in this section: cm=centimeter, g=grams, kGy=kiloGray, kV=kilovolt, L=liter, mL=milliliter, mm=millimeter, mM=millimolar, N=normal, NMR=nuclear magnetic resonance, ° C.=degrees Celsius, mol=moles, ppm=parts per million, and IR=infrared.

Materials Table

| Name | Description |
|---|---|
| Diacetone acrylamide | obtained from the Sigma-Aldrich Corporation, St. Louis, MO |
| initiator | 2,2'-azodi(2-methylbutyronitirile), free-radical initiator, sold under the trade designation "VAZO 67" from the Sigma-Aldrich Corporation |
| surfactant | Trimethylnonylpolyethylene glycol sold under the trade designation "TERGITOL TMN 10" from the Sigma-Aldrich Corporation |
| MAPTAC | [3-(Methacryloylamino)propyl]trimethylammonium chloride was obtained from Evonik Industies, Essen, Germany |
| Aminoguanidine hydrochloride | obtained from TCI America, Portland, OR |
| NVP | N-vinylpyrrolidone was obtained from Ashland Specialty Chemicals, Covington, KY |
| GMA | Glycidyl methacrylate was obtained from the Dow Chemical Company, Midland, MI |
| Staple Fibers I | Fibrillated polyethylene fibers available under the trade designation "SHORT STUFF Fibrillated HDPE" grade E380F, about 0.7 mm in length and 0.015 mm diameter from Minifibers Incorporated, Johnson City, TN |
| Staple Fibers II | Fibrillated polyethylene fibers available under the trade designation "SHORT STUFF Fibrillated HDPE" grade E780F, about 1.6 mm in length and 0.025 mm diameter from Minifibers Incorporated, Johnson City, TN |

Preparatory Example 1 [PE1; Guanylated Polyethylenimine (G-PEI)]

Polyethylenimine (PEI), Mw (molecular weight)=60,000 g/mole (100 grams of a 50 wt % solution in water; obtained from ACROS Organics, Geel, Belgium), was charged to a 1 L flask and deionized water (259 g) was added the flask to reduce the % solids content to about 25%. O-methylisourea hemisulfate (36.9 g) was added to the flask and the resulting solution was mechanically stirred at ambient temperature for about 20 hours. Analysis by NMR spectroscopy indicated conversion to the desired product having 25% of the amine groups of PEI (primarily the primary amine groups) converted to guanidines. Concentrated hydrochloric acid (38 g) was used to titrate the mixture to about pH 7 (measured using pH paper). Percent solids was determined to be 21.0% using a Mettler Toledo moisture balance analyzer (model number HR73, obtained from the Mettler Toledo Corporation, Columbus, OH).

Preparatory Example 2 [PE2; Poly(diacetoneacrylamide guanylhydrazone (pDAAGH)]

Diacetone acrylamide (160 g), ethanol (240 g) and initiator (0.8 g) were charged to a 1000 mL creased round bottomed 3-necked flask having a thermowell port. The reaction flask was equipped with overhead stirrer, nitrogen inlet and cold water condenser. The mixture was purged with a slow stream of nitrogen gas for 5 minutes and then heated at 60° C. (using a heating mantle) with stirring for 20 hours to convert the monomer to polymer. Ethanol (133 g) was added to dilute the polymer solution to about 30% by weight. A portion of this polymer solution (253.3 g) was placed in a round bottomed flask equipped with an overhead stirrer. Aminoguanidine hydrochloride (49.7 g) was dissolved in deionized water (150 g) and then added to the reaction flask. Concentrated hydrochloric acid (0.5 mL) was added and the solution was stirred for 20 hours at ambient temperature. IR spectroscopy and 41-NMR analyses confirmed the formation of poly(diacetoneacrylamide guanylhydrazone). The reaction mixture was sequentially submitted to vacuum in order to remove most of the ethanol; neutralized to pH 7 by the addition of 1 N NaOH; and finally adjusted to about 20% solids by the addition of deionized water.

Preparatory Example 3 [PE3; Poly(diallyldimethylammonium chloride) (pDADMAC)]

Poly(diallyldimethylammonium chloride) (pDADMAC) (average MW 400,000-500,000 g/mol, 20 weight % in water) solution was obtained from Sigma-Aldrich and was diluted to 10 weight % in deionized water.

Preparatory Example 4 (PE4)

Staple Fibers I (5 g) were placed in an open plastic bag and purged with nitrogen in an oxygen depleted (<20 ppm oxygen) glovebox. The bag containing the fibers was sealed.

A monomer grafting solution (150 grams) containing by weight 12% NVP, 10% MAPTAC, 4% GMA, 74% deionized water was added to a glass jar. The jar was capped and shaken by hand to mix the contents. The jar was then opened, and the solution was sparged with nitrogen for 2 minutes to remove any dissolved oxygen from the solution. The jar was re-capped and transferred into the oxygen depleted glovebox. The jar lid was then removed to flush any residual air from the jar headspace.

The sealed bag containing fibers was removed from the glove box and irradiated to a dose level of 40 kGy by passing through an Energy Sciences Incorporated CB-300 electron beam apparatus in a single pass operation at a speed of approximately 5.5 meters per minute and an accelerating voltage of 300 kV. The bag containing the irradiated fibers was then returned to the glove box.

The grafting solution was added to the bag containing the irradiated fibers and the sealed bag was maintained for 3 hours in the nitrogen purged glovebox. The resulting copolymer grafted fibers were washed three times with deionized water, allowing the water to drain through a screen mesh while retaining the fibers. The fibers were then transferred to a large aluminum pan and allowed to dry. After drying, any clumped fibers were separated using a blender on a low setting.

Preparatory Example 5 (PE5)

The same procedure as reported in Preparatory Example 4 was followed with the exception that 5 g of Staple Fibers II were used instead of Staple Fibers I.

Preparatory Example 6 (PE6)

The same procedure as reported in Preparatory Example 5 was followed with the exception that a different grafting solution (150 g) containing by weight 12% NVP, 10% MAPTAC, 0.4% TERGITOL TMN10, and 77.6% deionized water was used.

Preparatory Example 7 (PE7)

The same procedure as reported in Preparatory Example 5 was followed with the exception that a different grafting solution (150 g) containing by weight 12% NVP, 4% GMA, and 84% deionized water was used.

Preparatory Example 8 (PE8)

A copolymer grafted nonwoven substrate was prepared from a melt-blown polypropylene microfiber (PP) nonwoven substrate (characterized by a substrate thickness of 1.85 mm, an effective fiber diameter of 8 micrometers, a basis weight of 200 grams per square meter, and solidity of 10%). A sample of the melt-blown polypropylene microfiber nonwoven substrate (8.5 inches by 8.5 inches) was purged of air under a nitrogen atmosphere in a glove box. Once the oxygen levels reached <20 ppm, the nonwoven substrate was inserted into a plastic bag and sealed.

A monomer grafting solution (150 grams) containing by weight 12% NVP, 10% MAPTAC, 4% GMA, 74% deionized water was added to a glass jar. The jar was capped and shaken by hand to mix the contents. The jar was then opened, and the solution was sparged with nitrogen for 2 minutes to remove any dissolved oxygen from the solution. The jar was re-capped and transferred into the oxygen depleted glovebox. The jar lid was then removed to flush any residual air from the jar headspace.

The sealed bag containing nonwoven sample was removed from the glove box and irradiated to a dose level of 40 kGy by passing through an Energy Sciences Incorporated CB-300 electron beam apparatus in a single pass operation at a speed of approximately 5.5 meters per minute and an accelerating voltage of 300 kV. The bag containing the irradiated nonwoven sample was then returned to the glove box.

The monomer grafting solution was added to the plastic bag containing the nonwoven sample. The bag was sealed and the solution was distributed through the nonwoven sample using a hand roller so that the nonwoven sheet was uniformly covered with the solution. The bag was sealed and the nonwoven sample was maintained flat in the bag for 3 hours. The resulting copolymer grafted nonwoven sample was removed from the bag and boiled in deionized water for one hour. The sample was removed from the water bath and air dried at room temperature for 24 hours. Discs (25 mm in diameter) were punched from the dried sample for use.

Preparatory Example 9 (PE9)

Discs (25 mm in diameter) were punched from 3M ZETA PLUS SP Depth Filters (grade 05, obtained from the 3M Corporation, St. Paul, MN) for use.

CHO Cell Culture Fluid Preparation

A monoclonal antibody-producing Chinese hamster ovary (CHO) cell culture was produced using a fed-batch process over 10-12 days in a bioreactor (available under the trade designation READYTOPROCESS WAVE 25 from GE Healthcare, Chicago, IL). The culture was harvested at 80% viability into 2 L sterile media bottles. The harvested cell culture fluid was refrigerated overnight at 4° C. to settle cells and cell debris. Concentrated biomass was achieved by pumping supernatant out of the container. Packed cell volume (PCV) of the concentrated biomass was determined by centrifugation of 200 microliters of CHO cell culture with a fixed angle rotor down at 2,500 rcf (relative centrifugal force) for 1 minute in a PCV cell counting tube (obtained from Sigma-Aldrich). PCV was adjusted to the desired level using supernatant fluid. The CHO culture was stored at 4° C. for up to 3 days.

Method of Separating

Fifty milliliters of CHO cell culture fluid (8% PCV) was added to a glass beaker and stirred at 100 rpm using a magnetic stir-bar [SPINFIN magnetic stirring bar (22 mm diameter by 12.7 mm height) obtained from Bel-Art SP Scienceware, Wayne, NJ] and stir plate. The cationic polymer as specified was diluted in water to 10 weight %. The diluted polymer sample was added using a micro channel pipet to the stirring CHO cell culture over a period of 90 seconds to achieve a final concentration of 0.1 weight %. After 15 minutes of continued stirring, the resulting bio-polymer complex suspension was immediately submitted to a separating vessel (described below) for further processing.

Unless otherwise noted, the separating vessel was loosely packed with 1 g of fibers to a height of 3.175 cm in a separating vessel. The 1 g of fibers occupied a volume of 9 cubic centimeters giving a fiber density of 0.11 g/cm$^3$. The separating vessel contained a clear, polycarbonate vessel body (1.9 cm inner diameter and 5.1 cm height) with a cap attached to the top of the vessel body. The vessel cap contained an inlet port and a vent port. The bottom of the vessel contained an outlet port with a stopcock. The vessel was operated in a vertical direction, wherein the inlet was farthest from the Earth and the outlet was closest to the Earth. A pressure sensor was placed upstream of the inlet port. A 10 mL solution of Tris buffer (20 mM Tris-HCl, 50 mM NaCl, pH 8) was added to the vessel. Using a PendoTech (Princeton, NJ) normal flow filtration system with MASTERFLEX L/S PharMed BPTflex size 16 tubing (Cole-Parmer Company, Vernon Hills, IL) connected to the inlet port, the bio-polymer complex suspension was pumped at 2 mL/minute into the separating vessel. When the vessel was filled, the outlet port was then opened and the vent port was closed. Pumping was continued and the filtrate was collected through the outlet port into a conical receiving tube. The collection of the liquid exiting the outlet of the vessel (referred to as "filtrate") was stopped when either a) the inlet pressure reached 5 psi or b) when no visible liquid was observed in the separating device and no liquid was observed exiting the separating vessel over a two minute period.

Turbidity

The turbidity of the collected filtrate was measured using a Hach 2100AN Turbidimeter (Hach Company, Loveland, CO).

% Yield

Yield was determined by following equation:

$$\text{Yield (\%)}=[(\text{volume of filtrate recovered})/(\text{volume of cell culture liquid}+\text{volume of tris buffer})]\times 100.$$

The volume of cell culture liquid was determined by multiplying the initial volume of cell culture by the PCV value as expressed as a decimal.

Particle Size of Bio-Polymer Complex

Fifty milliliters of CHO cell culture fluid (8% PCV) was added to a glass beaker and stirred at 100 rpm using a magnetic stir bar [SPINFIN magnetic stirring bar (22 mm diameter by 12.7 mm height) obtained from Bel-Art SP Scienceware]. A single polymer selected from Preparatory Examples 1-3 was diluted in water to 10 weight %. The diluted polymer sample was added using a micro channel pipet to the stirring CHO cell culture over a period of 90 seconds to achieve a final concentration of 0.1 weight %. The mixture was stirred for 15 minutes while the particle size of the resulting bio-polymer complex was measured. A focused Beam Reflectance Measurement probe (Particle-Track G400; Mettler Toledo, Columbus, OH) was inserted 2 inches into the liquid so that it was not positioned in the vortex. Particle size was tracked and evaluated using iC FBRM 4.4 software (Mettler Toledo). The mean particle sizes (micrometers) measured at the 15 minute time point are reported in Table 1.

TABLE 1

| Cationic Polymer | Mean Particle Size of the Bio-Polymer Complex (micrometers) |
|---|---|
| PE1 (G-PEI) | 127 |
| PE2 (pDAAGH) | 81 |
| PE3 (pDADMAC) | 40 |

Example 1

The Method of Separating as described above was followed using G-PEI polymer of Preparatory Example 1 as the cationic polymer and the separating vessel was loosely packed with fibers of Preparatory Example 6 (1.0 g) to a height of 3.175 cm in a separating vessel. The 1 g of fibers occupied a volume of 9 cubic centimeters giving a fiber density of 0.11 g/cm$^3$. Two independent trials of the procedure were conducted and the mean results for yield (%) and turbidity (NTU) of the recovered filtrate are reported in Table 2 with the calculated standard deviations (n=2).

Example 2

The Method of Separating as described above was followed using Preparatory Example 2 (pDAAGH) as the cationic polymer and the separating vessel was loosely packed with fibers of Preparatory Example 6 (1.0 g) to a height of 3.175 cm in a separating vessel. The 1 g of fibers occupied a volume of 9 cubic centimeters giving a fiber density of 0.11 g/cm$^3$. A single trial was conducted and the results for yield (%) and turbidity (NTU) of the recovered filtrate are reported in Table 2.

Example 3

The Method of Separating as described above was followed using G-PEI polymer of Preparatory Example 1 as the cationic polymer and the separating vessel was loosely packed with fibers of Preparatory Example 6 (0.8 g) to a height of 5 cm in a separating vessel. The 0.8 g of fibers occupied a volume of 15 cubic centimeters giving a fiber density of 0.05 g/cm$^3$. A single trial was conducted and the results for yield (%) and turbidity (NTU) of the recovered filtrate are reported in Table 2.

Comparative Example A (CE A)

The Method of Separating as described above was followed using Preparatory Example 3 (pDADMAC) as the cationic polymer and the separating vessel was loosely packed with fibers of Preparatory Example 6 (1.0 g) to a height of 3.175 cm in a separating vessel. The 1 g of fibers occupied a volume of 9 cubic centimeters giving a fiber density of 0.11 g/cm$^3$. Two independent trials of the procedure were conducted and the mean results for yield (%) and turbidity (NTU) of the recovered filtrate are reported in Table 2 with the calculated standard deviations (n=2).

Comparative Example B (CE B)

The Method of Separating as described above was followed using G-PEI polymer of Preparatory Example 1 as the cationic polymer and the separating vessel was packed with fibers of Preparatory Example 6 (0.8 g) to a height of 1.2 cm in a separating vessel. The 0.8 g of fibers occupied a volume of 3.4 cubic centimeters giving a fiber density of 0.24 g/cm$^3$. A single trial was conducted and the results for yield (%) and turbidity (NTU) of the recovered filtrate are reported in Table 2. Collection of the filtrate was stopped due to the inlet pressure reaching 5 psi.

TABLE 2

| Example | Cationic Polymer | Fiber | Fiber Packing (g/cm$^3$) | Yield (%) | Turbidity of Filtrate (NTU) |
|---|---|---|---|---|---|
| 1 | PE1 (G-PEI) | PE6 | 0.11 | 87% ± 0.5% | 14 ± 3.3 |
| 2 | PE2 (pDAAGH) | PE6 | 0.11 | 69% | 3 |
| CE A | PE3 (pDADMAC) | PE6 | 0.11 | 94% ± 1.6% | 4289 ± 273 |
| 3 | PE1 (G-PEI) | PE6 | 0.05 | 87% | 13 |
| CE B | PE1 (G-PEI) | PE6 | 0.24 | 28% | 45 |

Examples 4-6

The Method of Separating as described above was followed using G-PEI polymer of Preparatory Example 1 as the cationic polymer and the separating vessel was filled with different copolymer grafted staple fibers as described in Table 3. Each of the staple fibers was placed at a height of 3.175 cm in the separation vessel, resulting in a volume of 9 cubic centimeters for each example. Since different masses of each sample were used, the fiber packing was different for each example. Example 4 used 1.0 g of PE4, Example 5 used 1.3 g of PE5, and Example 6 used 1.0 g of PE7, resulting in the fiber packing density is described in Table 3. A single trial was conducted for each example and the results for yield (%) and turbidity (NTU) of the recovered filtrate are reported in Table 3.

TABLE 3

| Example | Cationic Polymer | Fiber | Fiber Packing (g/cm$^3$) | Yield (%) | Turbidity of Filtrate (NTU) |
|---|---|---|---|---|---|
| 4 | PE1 (G-PEI) | PE4 | 0.11 | 87% | 20 |
| 5 | PE1 (G-PEI) | PE5 | 0.14 | 79% | 22 |
| 6 | PE1 (G-PEI) | PE7 | 0.11 | 82% | 17 |

Example 7

Example 6 as described above was repeated except that instead of immediately adding the bio-polymer complex suspension to the separating vessel, the bio-polymer complex suspension was allowed to settle for 10 minutes before the suspension was pumped into the separating vessel for further processing and the separation vessel used PE6 fibers. A single trial was conducted and the results for yield (%) and turbidity (NTU) of the recovered filtrate are reported in Table 4.

Example 8

The procedure as reported in Example 7 was followed with the exception that the polymer of Preparatory Example 2 (pDAAGH) was used instead of the G-PEI polymer of Preparatory Example 1. The results for yield (%) and turbidity (NTU) of the recovered filtrate are reported in Table 4.

Comparative Example C (CE C)

The procedure as reported in Example 7 was followed with the exception that the polymer of Preparatory Example 3 (pDADMAC) was used instead of the G-PEI polymer of Preparatory Example 1. A single trial was conducted and the results for yield (%) and turbidity (NTU) of the recovered filtrate are reported in Table 4.

TABLE 4

| Example | Cationic Polymer | Fiber | Fiber Packing (g/cm$^3$) | Yield (%) | Turbidity of Filtrate (NTU) |
|---|---|---|---|---|---|
| 7 | PE1 (G-PEI) | PE6 | 0.11 | 88% | 30 |
| 8 | PE2 (pDAAGH) | PE6 | 0.11 | 86% | 4 |
| CE C | PE3 (pDADMAC) | PE6 | 0.11 | 86% | 968 |

Comparative Example D (CE D)

The Method of Separating as described above was followed using G-PEI polymer of Preparatory Example 1 as the cationic polymer. Instead of the separating vessel packed with fibers, a 25 mm disc of copolymer grafted nonwoven from Preparatory Example 8 was inserted in the bottom of the separating vessel. The disc was held in place using o-rings. A 2 mL solution of Tris buffer solution (20 mM Tris-HCl, 50 mM NaCl, pH 8) was added to the vessel instead of the 10 mL as described in the Separation Method described above.

A single trial was conducted. Collection of the filtrate was stopped due to the inlet pressure reaching 5 psi. The results for yield (%) are reported in Table 5. Turbidity of the filtrate could not be measured, because an insufficient amount of filtrate was recovered for testing.

Comparative Example E (CE E)

The procedure as described in Comparative Example D was followed with the exception that the bio-polymer complex suspension was allowed to settle for 10 minutes before it was submitted to the separating vessel for further processing. A single trial was conducted and the results for yield (%) are reported in Table 5. Collection of the filtrate was stopped due to the inlet pressure reaching 5 psi. Turbidity of the filtrate could not be measured, because an insufficient amount of filtrate was recovered for testing.

Comparative Example F (CE F)

The procedure as described in Comparative Example D was followed with the exception that a disc from Preparatory Example 9 (PE9) was used instead of the disc from Preparatory Example 8 (PE8). A single trial was conducted and the results for yield (%) and turbidity are reported in Table 5. Collection of the filtrate was stopped due to the inlet pressure reaching 5 psi.

Comparative Example G (CE G)

The procedure as described in Comparative Example F was followed with the exception that the bio-polymer complex suspension was allowed to settle for 10 minutes before it was submitted to the separating vessel for further processing. A single trial was conducted and the results for yield (%) are reported in Table 5. Collection of the filtrate was stopped due to the inlet pressure reaching 5 psi. Turbidity of the filtrate could not be measured, because an insufficient amount of filtrate was recovered for testing.

TABLE 5

| Example | Cationic Polymer | Nonwoven Disc | Yield (%) | Turbidity of Filtrate (NTU) |
|---|---|---|---|---|
| CE D | PE1 (G-PEI) | PE8 | 8% | NM |
| CE E | PE1 (G-PEI) | PE8 | 3% | NM |
| CE F | PE1 (G-PEI) | PE9 | 43% | 25 |
| CE G | PE1 (G-PEI) | PE9 | 3% | NM |

NM = not measured

Foreseeable modifications and alterations of this invention will be apparent to those skilled in the art without departing from the scope and spirit of this invention. This invention should not be restricted to the embodiments that are set forth in this application for illustrative purposes. To the extent that there is any conflict or discrepancy between this specification as written and the disclosure in any document mentioned or incorporated by reference herein, this specification as written will prevail.

What is claimed is:

1. A method of purifying a target non-binding molecule from an aqueous biological composition comprising a binding species, the method comprising:

(a) contacting a cationic polymer and the aqueous biological composition to form a mixture comprising a bio-polymer complex and the target non-binding molecule in a liquid, wherein the bio-polymer complex has an average particle diameter of at least 45 micrometers, (b) adding the mixture to a filtering volume of a vessel, wherein the vessel comprises loosely packed staple fibers;

(c) allowing the mixture to separate through the loosely packed staple fibers; and (d) collecting a filtrate comprising the target non-binding molecule;

wherein said loosely packed staple fibers are not cationically functionalized.

2. The method of claim 1, wherein the loosely packed staple fibers have a packing density of at least 0.03 g/cm$^3$.

3. The method of claim 1, wherein the loosely packed staple fibers have a packing density of at most 0.24 g/cm$^3$.

4. The method of claim 1, wherein the cationic polymer is a water soluble or water dispersible polymer.

5. The method of claim 1, wherein the cationic polymer is functionalized with guanidinyl groups.

6. The method of claim 5, wherein the cationic polymer comprises groups of the formula:

$$—[C(R^1)═N—R^2]_n—N(R^3)—[C(═N—R^4)N(R^4)]_m—R^5$$

wherein $R^1$ is a H, C1-C12 alkyl, C5-C12 (hetero)aryl, or a residue of the polymer chain;

$R^2$ is a covalent bond, a C2-C12 (hetero)alkylene, or a C5-C12 (hetero)arylene;

$R^3$ is H, C1-C12 alkyl, or C5-C12 (hetero)aryl; and each $R^4$ is independently H, C1-C12 alkyl or alkylene, C5-C12 (hetero)aryl or (hetero) arylene, cyano, or —C(═NH)—N($R^2$)-Polymer;

$R^5$ is H, C1-C12 (hetero)alkyl, C5-C12 (hetero)alkyl, or —N($R^4$)$_2$;

n is 0 or 1; and m is 1 or 2.

7. The method of claim 1, wherein the cationic polymer is further functionalized with quaternary ammonium groups.

8. The method of claim 1, wherein the cationic polymer is derived from an amino polymer, optionally, wherein the amino polymer is selected from the group consisting of polyethylenimine, polylysine, polyaminoamides, polyallylamine, polyvinylamine, polydimethylamine-epichlorohydrin-ethylenediamine, and dendrimers formed from polyamidoamine (PAMAM) and polypropylenimine.

9. The method of claim 8, wherein 0.1 to 100 mole percent of the available amino groups of the amino polymer are functionalized with guanidinyl groups, optionally, wherein the guanidinyl groups are in the amino polymer chain.

10. The method of claim 1, wherein the cationic polymer is derived from a carbonyl polymer, optionally, wherein the carbonyl polymer is selected from the group consisting of; acrolein, vinyl methyl ketone, vinyl ethyl ketone, vinyl isobutyl ketone, diacetone (meth)acrylamide, acetonyl acrylate, carbon monoxide copolymer, and diacetone (meth) acrylate (co)polymers.

11. The method of claim 1, wherein 0.1 to 10,000 micrograms of cationic polymer is added per mL of the aqueous biological composition.

12. The method of claim 1, wherein the bio-polymer complex has an average particle diameter of at most 200 micrometers.

13. The method of claim 1, further comprising suspending the bio-polymer complex in the liquid prior to addition to the vessel.

14. The method of claim 1, wherein immediately following step (a), the biopolymer complex is added to the filtering volume of the vessel.

15. The method of claim 13, wherein suspending the bio-polymer complex in the liquid comprises agitating the bio-polymer complex in the liquid.

16. The method of claim 1, wherein at least a portion of the loosely packed staple fibers are hydrophilic.

17. The method of claim 1, wherein at least a portion of the loosely packed staple fibers are fibrillated.

18. A kit comprising:

(a) plurality of staple fibers wherein the staple fibers are loosely packed in a bed; and (b) a cationic polymer;

wherein said staple fibers are not cationically functionalized.

19. The kit of claim 18, wherein the packing density of the fibers in the bed is at least 0.03 $g/cm^3$ and at most 0.24 $g/cm^3$.

* * * * *